(12) United States Patent
Martinez et al.

(10) Patent No.: US 7,541,196 B2
(45) Date of Patent: *Jun. 2, 2009

(54) PLANAR OPTICAL WAVEGUIDE BASED SANDWICH ASSAY SENSORS AND PROCESSES FOR THE DETECTION OF BIOLOGICAL TARGETS INCLUDING EARLY DETECTION OF CANCERS

(75) Inventors: Jennifer S. Martinez, Santa Fe, NM (US); Basil I. Swanson, Los Alamos, NM (US); John E. Shively, Arcadia, CA (US); Lin Li, Monrovia, CA (US)

(73) Assignee: Los Alamos National Security, LLC, Los Alamos, NM (US)

( * ) Notice: Subject to any disclaimer, the term of this patent is extended or adjusted under 35 U.S.C. 154(b) by 229 days.

This patent is subject to a terminal disclaimer.

(21) Appl. No.: 11/172,244

(22) Filed: Jun. 29, 2005

(65) Prior Publication Data

US 2006/0019321 A1    Jan. 26, 2006

Related U.S. Application Data

(60) Provisional application No. 60/583,911, filed on Jun. 29, 2004.

(51) Int. Cl.
*G01N 33/551* (2006.01)
(52) U.S. Cl. .............. 436/524; 422/82.05; 422/82.11; 435/5; 435/6; 435/7.2; 435/287.2; 435/288.7; 436/164; 436/172; 436/805

(58) Field of Classification Search .................. None
See application file for complete search history.

(56) References Cited

U.S. PATENT DOCUMENTS 5,830,766 A * 11/1998 Attridge et al. ............. 436/518

\* cited by examiner

*Primary Examiner*—Christopher L Chin
(74) *Attorney, Agent, or Firm*—Bruce H. Cottrell; Juliet A. Jones

(57) ABSTRACT

An assay element is described including recognition ligands adapted for binding to carcinoembryonic antigen (CEA) bound to a film on a single mode planar optical waveguide, the film from the group of a membrane, a polymerized bilayer membrane, and a self-assembled monolayer containing polyethylene glycol or polypropylene glycol groups therein and an assay process for detecting the presence of CEA is described including injecting a possible CEA-containing sample into a sensor cell including the assay element, maintaining the sample within the sensor cell for time sufficient for binding to occur between CEA present within the sample and the recognition ligands, injecting a solution including a reporter ligand into the sensor cell; and, interrogating the sample within the sensor cell with excitation light from the waveguide, the excitation light provided by an evanescent field of the single mode penetrating into the biological target-containing sample to a distance of less than about 200 nanometers from the waveguide thereby exciting any bound reporter ligand within a distance of less than about 200 nanometers from the waveguide and resulting in a detectable signal.

25 Claims, 3 Drawing Sheets

PLANAR OPTICAL WAVEGUIDE BASED SANDWICH ASSAY SENSORS AND PROCESSES FOR THE DETECTION OF BIOLOGICAL TARGETS INCLUDING EARLY DETECTION OF CANCERS

This application claims the benefit of U.S. Provisional Application Ser. No. 60/583,911 filed on Jun. 29, 2004.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to sandwich assay processes and to a thin film supported sandwich assay element on a single mode planar optical waveguide. Such an assay can provide a means of detecting and quantifying proteins and the like for medical diagnostics such as early detection of cancer.

BACKGROUND OF THE INVENTION

The detection of trace amounts of biologically significant compounds, such as steroids, drugs, selected antigens, or tumor markers, is often accomplished inexpensively by the employment of an immunoassay. Enzyme immunoassay (EIA) methods are common antigen detection techniques. One of the most common types of immunoassays is the Enzyme-Linked Immunosorbant Assay (ELISA), a solid phase enzyme immunoassay technique. Such assays rely on an immunogenic recognition of a substance in question followed by the amplification of the signal generated by that recognition. Enzymes are widely used in immunoassays as the amplifier of the antibody-antigen recognition event. Traditionally, antigen capture assays involve the application of an antigen-containing sample to a plastic plate where a "capture" antibody has been previously bound. A secondary ("detection") antibody is then applied and binds to the antigen. This binding forms a sandwich that leads to the quantification of antigen present. EIAs are easy to multiplex and the use of more than one antibody in the sandwich assay improves the specificity of the test by requiring two specific interactions before signal is detected.

ELISA may be preformed in a number of different ways. The two most common are the competitive mode and the sandwich assay. In a competitive mode ELISA, a surface, usually either a polystyrene plate or a nitrocellulose membrane, is coated with a capture antigen. These surfaces are normally chosen because they bind protein non-specifically. Therefore, if the antigen is not a protein, it may be covalently linked to a carrier protein and bound to the surface without further chemistry. After the antigen is bound, the remaining binding sites on the surface are blocked with another protein as a blocking agent. Then the test fluid and enzyme-labeled antibody are added. If no antigen is in the test fluid, the labeled antibody will bind to the antigen adsorbed on the surface. Conversely, if antigen is present in the test fluid, the antigen will block the binding sites on the enzyme-labeled antibody and prevent it from binding to the antigen adsorbed on the surface. The surface is washed to remove unbound materials, and a substrate is added for the enzyme. The enzyme catalyzes a reaction in which the substrate reacts to form a colored material that can be quantitatively measured with a spectrophotometer. The intensity of the color produced is proportional to the enzyme activity and the amount of antibody bound, which is inversely proportional to the amount of antigen in the test fluid.

In a sandwich assay ELISA, an antibody that recognizes part of the antigen is bound to a surface. Since antibodies are proteins, this is readily accomplished by allowing the surface to contact a solution of the antibody. As in the competitive ELISA, the remaining sites on the surface are blocked with another protein as a blocking agent. The test fluid is then added. If an antigen is present in the test fluid, the antibody on the surface will capture the antigen. Then a second, enzyme-labeled antibody, which recognizes a different part of the antigen than the first antibody, is added. The second antibody will then bind to the antigen that is captured on the surface. After washing the surface to remove any unbound materials, a substrate for the enzyme is added and the color produced is measured spectrophotometrically. In this form of an ELISA, the signal is directly proportional to the concentration of the antigen in a test sample. Such a sandwich assay is widely used in the commercial arena, e.g., for home pregnancy tests.

In either type of ELISA, the enzyme acts as the amplifier of the antigen-antibody reaction. That is, a color or other signal, such as light from some chemiluminescent reaction, is produced that can be observed macroscopically. Without this amplification step, the sensitivity of an immunoassay would be orders of magnitude less.

Several problems occur in the use of enzymes as amplifiers in immunoassays including:

1) Any change in enzyme activity will affect the precision of the assay. For example, loss of half of the activity of the enzyme in a competitive ELISA may produce a false positive since a smaller signal indicates the presence of the test substance. Since enzyme activity is sensitive to storage conditions, enzymes must be kept either refrigerated, freeze-dried or both. Also, controls must be performed to constantly test the activity of the enzyme. Inevitably, the shelf-life is limited by the stability of the enzyme.

2) Enzymes are expensive as they are derived from living sources and require substantial processing costs. The least expensive enzyme, on an activity basis, is Horseradish Peroxidase, which is, not surprisingly, the most common enzyme used in ELISAs. However, even Horseradish Peroxidase costs about $5/mg or $5000/g. Fortunately, very little enzyme is necessary for each assay.

3) The labeling of antibodies with enzymes is often a quite laborious procedure, as one must ensure that little unbound enzyme is present. If significant amounts of unbound enzyme are present or significant amounts of unlabeled antibody are present, the sensitivity of the ELISA is reduced.

4) Enzymes are often heterogeneous materials due to their isolation from natural sources. Therefore, characterization of enzyme-antibody conjugates can be difficult.

Although EIAs performed on 96-well plates are popular in the academic lab, modern clinical labs employ more highly automated assay systems. One example is the Abbott disposable IMx® cartridge system, which utilizes fluorescent polarization. In this approach, a capture antibody is bound to a microparticle, and the sample is incubated with the filter and a fluorescently labeled detection antibody. Since the unbound detection antibody has no net fluorescent polarization compared to the bound detection antibody, the fluorescent polarization signal is proportional to the amount of bound sample. Although this assay system does not employ an enzymatic amplification step, it is still very sensitive, and it has other advantages, including the elimination of time consuming wash steps.

Other automated systems involve other approaches to save time, such as using kinetic rather than equilibrium approaches to measure product. Other detection systems include exotic methods such as electrochemiluminescence (ECL), where the capture antibody is bound to magnetic beads and the detection antibody is labeled with a Ru(bipyridyl)$_3$ complex. After incubation and washing, the ruthenium complex emits light in an electrochemical cell. This assay system can detect antigens in the low picomolar (pM) range. All the above assay systems are performed in clinical labs on expensive equipment and are not available as physician operated desktop systems with untrained professionals.

SUMMARY OF THE INVENTION

To achieve the foregoing and other objects, and in accordance with the purposes of the present invention, as embodied and broadly described herein, the present invention provides a sandwich assay sensor element including recognition ligands for carcinoembryonic antigen (CEA) bound to a film on a single mode planar optical waveguide, the film from the group of a membrane, a polymerized bilayer membrane, and a self-assembled monolayer containing polyethylene glycol or polypropylene glycol groups therein.

The present invention further provides a sandwich assay process including: injecting a biological target-containing sample into a sensor cell including recognition ligands for carcinoembryonic antigen (CEA) bound to a film on a single mode planar optical waveguide, the film from the group of a membrane, a polymerized bilayer membrane, and a self-assembled monolayer containing polyethylene glycol or polypropylene glycol groups therein, the recognition ligands adapted for binding to CEA; maintaining the biological target-containing sample within the sensor cell for a time sufficient for a binding event to occur between CEA within the sample and the recognition ligands adapted for binding to CEA; injecting a solution into the sensor cell, the solution including a reporter ligand adapted for binding to bound CEA; and, interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal.

In another embodiment, the present method provides an assay process including: injecting a solution including an biological target-containing sample and a reporter ligand into a sensor cell including recognition ligands bound to a film on a single mode planar optical waveguide, the film from the group of a membrane, a polymerized bilayer membrane, and a self-assembled monolayer containing polyethylene glycol or polypropylene glycol groups therein, both the recognition ligands and reporter ligands adapted for binding to CEA; maintaining the biological target-containing sample within the sensor cell for a time sufficient for a binding event to occur between CEA within the sample and the recognition ligands adapted for binding to CEA and a time sufficient for a binding event to occur between CEA within the sample and the reporter ligand; injecting a wash solution into the sensor cell to remove excess biological target and excess reporter ligand; and, interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal.

DETAILED DESCRIPTION

The present invention concerns sandwich assay processes using a single mode planar optical waveguide and thin film supported sandwich assay elements on a single 1.5 mode planar optical waveguide. The use of sandwich assays on single mode waveguides takes advantage of the relatively high intensity of the evanescent field at the surface of the waveguide, as the detection molecules are well within the strong portion of the evanescent field, especially during the detection of a biological target such as CEA.

Figure 1:
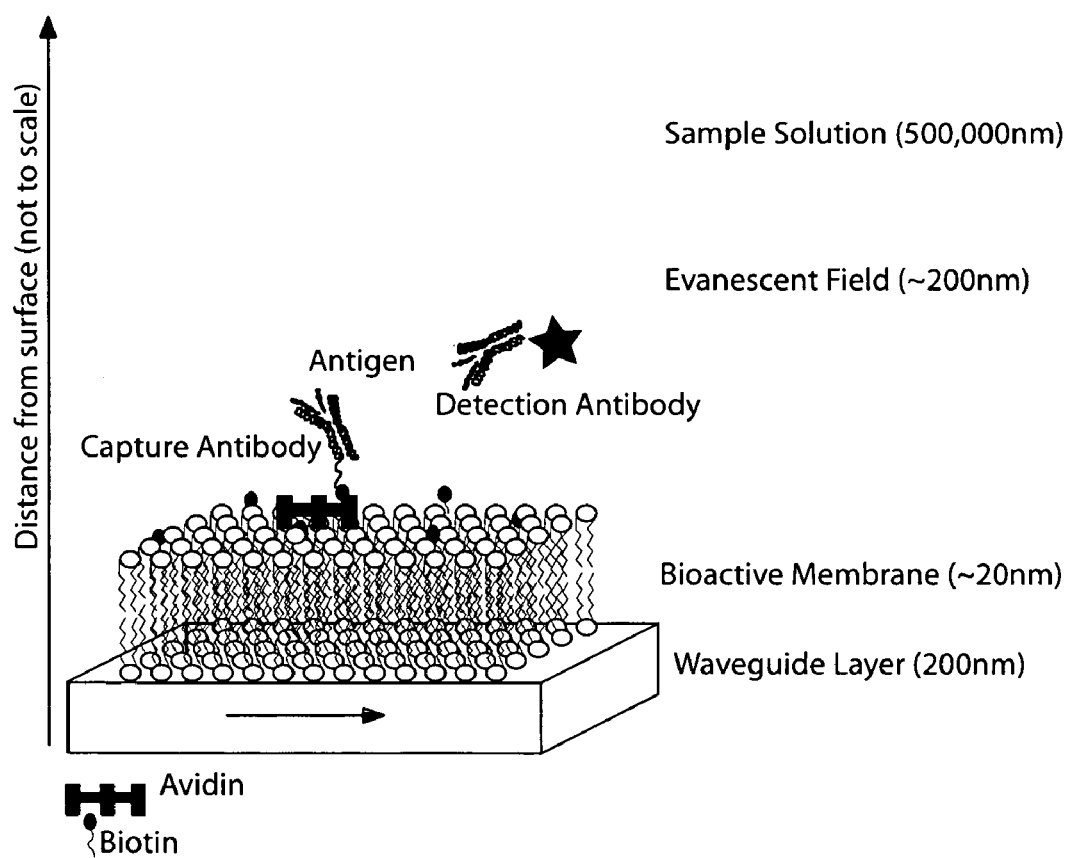
FIG. 1 illustrates a membrane-based sandwich assay where a recognition ligand, e.g., a capture antibody, is conjugated to a lipid molecule that anchors the antibody to the upper surface of a lipid bilayer. Exposure to an antigen (A) followed by a wash step and exposure to a reporter ligand, e.g., a fluorescent labeled reporter ligand, results in formation of the sandwich.

The base substrate in the present invention is a waveguide, preferably a single 20 mode planar optical waveguide. Single mode waveguides can be generally formed from thin (generally from about 100 to 150 nm in thickness) high index of refraction dielectric materials deposited upon a substrate having a much lower refractive index. Use of a waveguide can eliminate some problems related to background autofluorescence from complex samples and Raman scattering from water. Preferably, the waveguide surfaces will be of a material that can be employed to attach an intervening thin film material, such materials including, e.g., silica, silicon nitride, titania, mixtures of silica and silicon nitride often referred to as SiON, and the like. The materials used for the waveguide can also be a sol-gel material. FIG. 1 shows a single mode waveguide where (describe parts of waveguide with numbers). Diffraction gratings, etched into the substrate, provide a facile 30 method of coupling laser light into the thin waveguide film. Although most of the laser light is contained within the guided mode, a small portion (the evanescent field) extends out into the substrate and into the medium, which includes the biological sample. This evanescent filed falls off exponentially as the distance from the waveguide surface increases, and is effectively zero at a distance of less than half the wavelength of the coupled light.

The present invention involves the use of recognition ligands bound to a film on the base substrate or waveguide. By "recognition ligand" is meant any compound, composition, molecule or ligand capable of recognizing and having a binding affinity for a specific target such as CEA. Natural recognition molecules include antibodies, enzymes, lectins, and the like. For example, the recognition molecule for an antigen is an antibody while the recognition molecule for an antibody is either an anti-antibody or preferably, the antigen recognized by that particular antibody.

In sandwich assay sensors such as the present invention, recognition ligands are sometimes referred to as capture ligands. Among such ligands capable of recognizing and having a binding affinity for a specific target such as CEA are biomolecules such as antibodies, antibody fragments, i.e., a portion of a full length antibody such as, e.g., Fab, Fab', $F(ab')_2$, or Fv fragments and the like, recombinant or genetically engineered antibody fragments, e.g., diabodies, minibodies and the like. Other suitable recognition ligands may include peptides, single chain Fv molecules (scFv), peptides and mimetics thereof, carbohydrates, sugars and mimetics thereof, oligosaccharides, proteins, nucleotides and analogs thereof, aptamers, affinity proteins, small molecule ligands, receptor groups and monomers of multimers of each, i.e., multidentate ligands. Mixtures of such recognition ligands may be used as well.

Particular examples of antibodies useful in the present invention include T84.1-E3 and T84.66-A3.1-H11 described in: U.S. Pat. No. 4,873,313 by Crawford et al., for "Specific Hybridoma Cell Line and Monoclonal Antibodies Produced From Such Specific Hybridoma Cell Line and Method of Using Such Monoclonal Antibodies to Detect Carcinoembryonic Antigens"; the Journal of Immunology, "Monoclonal Antibodies for Carcinoembryonic Antigen and Related Antigens as a Model System: A Systematic Approach for the Determination of Epitope Specificities of Monoclonal Antibodies", vol. 130, no. 5, pp. 2308-2315 (1983), by Wagener et al.; and, the Journal of Immunology, "Monoclonal Antibodies for Carcinoembryonic Antigen and Related Antigens As a Model System: Determination of Affinities and Specificities of Monoclonal Antibodies by Using Biotin-Labeled Antibodies and Avidin as Precipitating Agent in a Solution Phase Immunoassay", vol. 130, no. 5, pp. 2302-2307 (1983), by Wagener et al., such descriptions incorporated herein by reference.

A recognition ligand can also be attached to a material that can be fluorescent, such as organic fluorophores, quantum dots or other fluorescent particles, or attached to silica or other suitable particles for scatter product detection. The attached material whether the fluorescent material or the material suitable for scatter product detection is often referred to as a reporter, e.g., a reporter ligand. Such attached materials provide a signaling function or a reporting function. The present invention also involves the addition of a recognition ligand/reporter ligand to the sensor system following reaction of the recognition or capture ligands with any target biomolecule. By "recognition ligand/reporter ligand" is meant a ligand capable of recognizing and having a binding affinity for a specific target such as a biomolecule, the ligand also providing the signaling or reporting function. Mixtures of such recognition ligand/reporter ligands may be used as well.

The recognition ligands and recognition ligand/reporter ligands are suitable for binding with selected biological targets such as CEA. Among suitable recognition ligands are included antibodies such as capture antibodies that can bind with selected antigen partners.

The base substrate includes a film thereon, the film being a bilayer membrane, a hybrid bilayer membrane, a polymerized bilayer membrane, or a self assembled monolayer (SAM) containing polyethylene glycol or polypropylene glycol groups therein. The term "polymerized membrane" refers to membranes that have undergone partial or complete polymerization. One example of a polymerized membrane can be polymerized phospholipids prepared from polymerizable monomaniac groups as shown, e.g., in U.S. Pat. No. 6,699,952.

By "membrane" is generally meant supported bilayers where membrane layers are deposited upon a support surface, hybrid bilayers where a first layer is covalently attached to an oxide surface, tethered bilayers where a membrane molecule is covalently bonded to the oxide substrate, or bilayers cushioned by a polymer film. Supported membranes useful in the practice of the present invention are generally described by Sackmann, in "Supported Membranes: Scientific and Practical Applications", Science, vol. 271, no. 5245, pp. 43-45, Jan. 5, 1996.

A self assembled monolayer can be attached to the substrate as follows: solution or vapor deposition using siloxane groups such as octadecyltrichlorosilane (OTS) or by Langmuir-Blodgett assembly using a LB trough.

The lipid components that can be used for the membrane layers in the present invention are generally described in the literature. Generally, these are phospholipids, such as, for example, phosphatidylcholines, phosphatidylethanolamines, phosphatidylglycerols, phosphatidylserines, phosphatidic acids, phosphatidylinositols or sphingolipids.

The recognition ligands can be linked or bound through various molecules to the film on the waveguide surface. Among suitable linking molecules can be various biotin-avidin linkages such as biotinylated lipids, and trifunctional linker molecules as described by Schmidt et al., U.S. Ser. No. 10/104,158, "Generic Membrane Anchoring System", filed on Mar. 21, 2002, such description incorporated herein by reference. Such trifunctional linker molecules can include membrane anchoring groups where the film is a membrane. Such trifunctional linker molecules can be preferable where a reference dye is desired to be incorporated into the system by addition onto one arm of the trifunctional linker molecules. This can serve to minimize background by comparison with the dye label on the sandwich assay. Such trifunctional linkers may also have a secondary recognition ligand in addition to the primary recognition ligand. The use of a secondary recognition ligand that binds an orthogonal epitope relative to the primary recognition ligand can serve to enhance the effective binding affinity thereby increasing the overall sensitivity of the assay.

The sandwich assay process of the present invention can be used for the determination, either qualitative or, mostly, quantitative, of biomolecules, such as carcinoembyronic antigen (CEA) and thus used for diagnosis and monitoring of cancer. By monitoring, it may be possible to distinguish between invasive and non-invasive cancers, e.g., between ductal carcinoma insitu (DCIS) from invasive ductal carcinoma. This may help guide further treatment of such cancers.

Assay sensitivities are partially determined by the affinity of the antibody for the antigen. It is desirable that sensitive antibodies should have a $K_d$ of at least 0.1-10 nM. The availability of two or more binding sites on a single antigen increases the apparent affinity of the interaction, by decreasing the off-rate of the antigen-antibody complex.

Formation of a bilayer membrane upon the waveguide surface can be accomplished by vesicle fusion, a process well known to those skilled in the art. Formation of either supported bilayer or hybrid bilayer membranes can also be accomplished using Langmuir-Blodgett techniques.

In the process of the present invention, dye-labeled reporter ligands are used to bring a dye reporter into the proximity of the interrogation field such that a signal can be obtained. Such reporter ligands are suitable for binding with the selected biological target following the binding of the selected biological target with the recognition ligand. Suitable reporter ligands can be antibodies that can bind with selected antigen partners.

Suitable dyes for the reporter ligand can include fluorophores such as, but not limited to, fluorescein, cadaverine, Texas Red™ (Molecular Probes, Eugene, Oreg.) and Cyanine 5™ (BDS, Pennsylvania). Generally, any fluorophore will typically be detectable in the visible to near infrared range, although other ranges may be used as well, as can dye encapsulated silica particles. Quantum dots and nanoshell materials can also be used as reporter dyes. In addition, scatter molecules such as selected metal, semiconductor or magnetic nanoparticles attached to oligonucleotides as described, e.g., by Mirkin et al., U.S. Pat. No. 6,903,207, such description incorporated herein by reference, may be used as well.

Interrogation of the sandwich assay in the process of the present invention is generally conducted at specific wavelengths selected to minimize or substantially eliminate background signal. By using the evanescent field from the waveguide, excitation light for the dye will only penetrate a short distance into the sample, generally less than about 200 nm. Within that distance, any bound biological target would also have the reporter ligand attached, but background would be minimized as little or no unbound dye label would be present.

The sensor and process of the present invention can provide high sensitivities and specificities. In some instances, detection of biological targets at levels as low as from about 100 femptomolar (fM) to about 1 pM can be obtained.

In one embodiment of the present invention, capture antibodies (as the recognition ligands) are conjugated to membrane anchoring molecules that anchor the capture antibodies to the upper fluid leaf of a phospholipid bilayer coating the surface of a single mode planar optical waveguide (see FIG. 1). Although shown configured using a fluid membrane, self assembled monolayers or other stable supported architectures such as polymerized bilayer membranes could be utilized as well. Laser excitation is coupled into the single mode waveguide through a grating structure that is imbedded onto the waveguide/substrate interface. A sample containing the biological target to be detected, e.g., an antigen, is then injected into the cell and allowed to incubate for a brief period of time (about 5 minutes) to permit binding of the biological target to the capture antibody. The sample is then replaced with buffer solution to wash away excess antigen. This wash step is followed by injection of a buffer solution containing a reporter ligand that has been labeled with a fluorescent molecule, e.g., an organic dye, an inorganic dye, a quantum dot or the like. The excitation light from the evanescent field of the single mode guided by the waveguide only penetrates a short distance (less than about 200 nm) into the sample, but this is adequate to excite the dye on the reporter ligand generating a fluorescence signal that is then detected, e.g., by a miniaturized fiber optic spectrometer that images the waveguide streak. In the absence of detectable antigen, little or no signal is generated in the spectral region of the reporter fluorescence.

Figure 3:
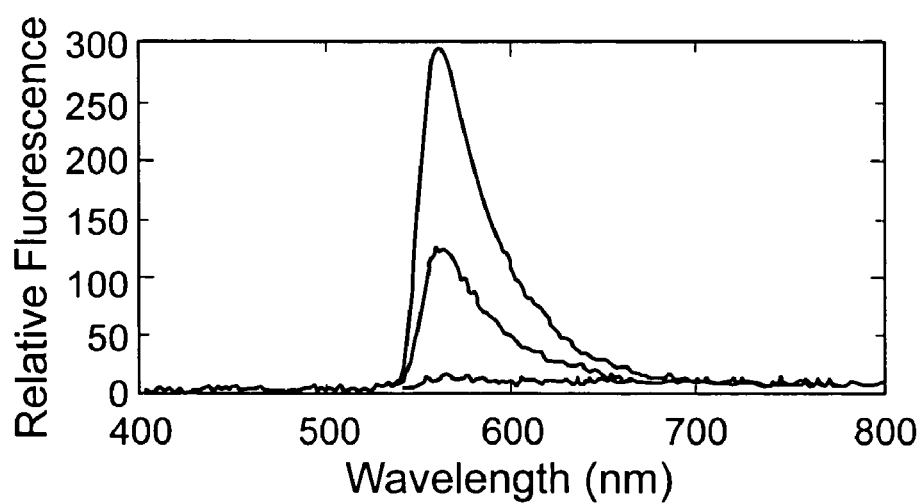
FIG. 3 shows a graph of the spectral response of a membrane sandwich assay on a waveguide surface to a sample containing CEA in accordance with the present invention.

In one embodiment, the present invention can be operated using a bench-top waveguide-based sensor system as described by Grace et al. in U.S. Pat. No. 6,801,677, "Waveguide-Based Optical Chemical Sensor", such description incorporated herein by reference. In another embodiment, the present invention can be operated using an optical waveguide-based biosensor system as described by Grace et al. in U.S. Ser. No. 10/842,750, "Integrated Optical Biosensor System", filed on May 11, 2004, such description incorporated herein by reference. The present invention can measure antigen, e.g., CEA, present in a buffer or serum, e.g., biological materials or environmental sample. Measurements can be performed using suitable recognition ligands and recognition ligand/reporter ligands for these markers. Different spectral response is expected for different samples as shown in FIG. 3. In each of these measurements, the incubation times for exposure to the sample and subsequent exposure to a recognition ligand/reporter ligand can be limited to five minutes each. The overall assay can be performed in as little as 10 minutes using the automated system. It is noteworthy to compare the results obtainable by the present invention to the results of commercial ELISA methods. The commercial ELISA assay takes at least 3 to 5 hours whereas the waveguide-based assay of the present invention can be completed in less than about 10 minutes.

In the preparation of the membrane sandwich assay structure in accordance with the present invention, the recognition ligand (capture antibody) can be anchored to the surface of a membrane using a biotin-avidin sandwich prepared as follows. The capture antibody can be conjugated to biotin using a biotin-ester molecule such as EZ-link Sulfo-NHS-LC-LC-biotin (commercially available from Pierce Chem. Co., Rockford, Ill.). A membrane can be fused onto the surface of the waveguide from a lipid mixture including, e.g., 1,2-Dioleoyl-sn-Glycero-3-Phosphocholine (DOPC) and a biotinylated lipid such as 1,2-Dipalmitoyl-sn-Glycero-3-Phosphoethanolamine-N-(Biotinyl) (commercially available from Avanti Polar Lipids, Alabaster, Ala.) using standard vesicle fusion techniques. The membrane on the waveguide surface can then be exposed to a solution of avidin and allowed to incubate for 5 minutes. Following rinsing by PBS, the biotinylated antibody can be added and incubated for 5 minutes. A sample cell containing the active membrane can then be ready for exposure to a sample.

Figure 2:
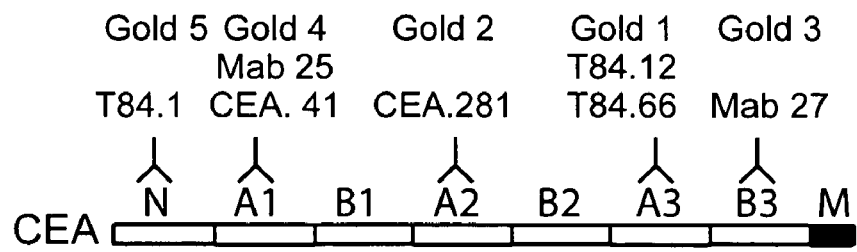
FIG. 2 shows the domain structure and epitope map of antibodies for carcinoembrionic antigen (CEA), a biological target that can be detected in accordance with the present invention.

In one embodiment, the present invention has been demonstrated using a sandwich assay structure in accordance with the present invention using antibodies for the N and A3 domains of CEA, specifically T84.1-E3 (T84.1) and T84.66-A3.1-H11 (T84.66). The T84.66 antibodies are described in U.S. Pat. No. 4,873,313 and have been deposited with the American Type Culture Collection and are identified by the designation HB8747, while the T84.1 antibodies are also shown in U.S. Pat. No. 4,873,313 and the Journal of Immunology references described previously. The domain structure and epitope map for antibodies to CEA are shown in FIG. 2. In the presently shown results, monoclonal antibodies (mAb T84.1) for the N domain have been used as the recognition ligands (capture antibodies) and monoclonal antibodies (mAb T84.66) for the A3 domain used for the reporter ligand. This may be reversed, if desired, or other recognition ligands and reporter ligands may be used for differing epitopes of any target.

For sensor system development and optimization and for the demonstration of the CEA assay on waveguides, a portable test-bed system has been designed. As a light source, a stabilized 532 nm frequency doubled yttrium orthovanadate laser was used. Laser light is coupled into the waveguide by positioning the excitation beam onto the diffraction grating at the appropriate angle of impingement.

The waveguide was coated with lipid membranes having biotin-avidin conjugated antibodies in the upper fluid leaf and was placed within a simple fluid cell. This cell was mounted in the sample cartridge and was irradiated as generally described above. An Ocean Optics fiber optic spectrometer was used, and it was positioned normal to the waveguide surface to collect the isotropic emission from the waveguide. The optical components were mounted onto a 12 inch by 12 inch by 0.5 inch optical bench. The test bed allowed the simple removal and installation of the sample cartridge without realignment of the optical train. The final component of this system was a PC based user interface for instrument control, data acquisition and analysis. Such a portable system permits precise measurements against various pathogens and protein markers.

Waveguides bearing bilayers containing the biotinylated lipid were placed into the flow cell of the waveguide apparatus and blocked with 2% bovine serum albumin (BSA) to minimize non-specific binding. The recognition ligand (capture antibody), a sample including CEA, and a fluorescent labeled reporter ligand (detection antibody) were sequentially added and individually incubated for five minutes (for a total of 15 minutes). The detection antibody was excited (532 nm) and the emission (whole spectra) detected by a miniaturized fiber optic spectrometer coupled to the existing optical waveguide test bed instrument. Buffer samples (PBS and 0.5% BSA) without CEA were used as negative controls. Both the negative and positive controls were exposed to the detection antibody.

Figure 4:
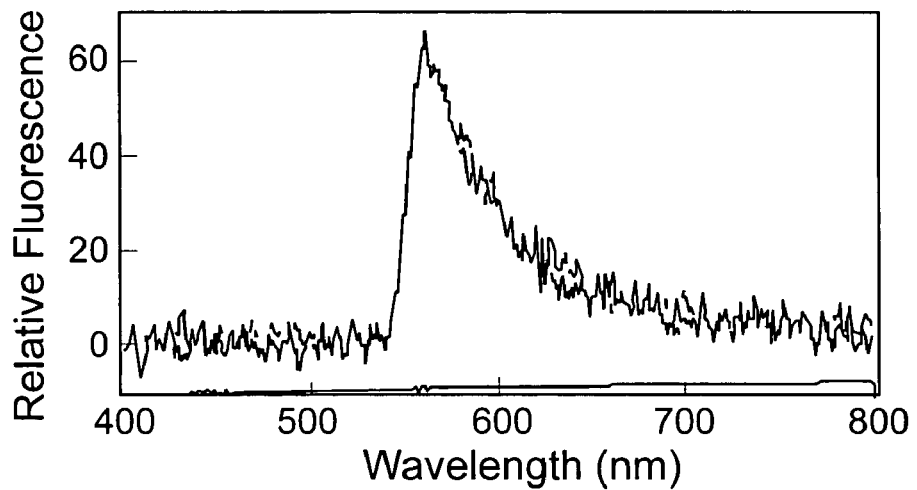
FIG. 4 shows a graph of the spectral response for nonspecific binding by a fluorescent labeled reporter ligand to a waveguide surface in accordance with the present invention in the absence of CEA.
Figure 5:
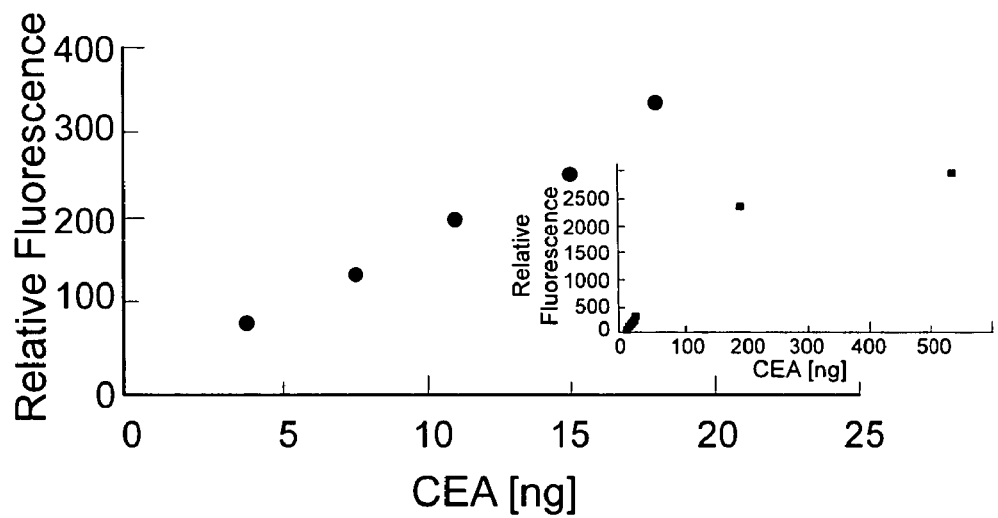
FIG. 5 shows a linearity of response for CEA on optical waveguides in accordance with the present invention.

The top curve of FIG. 3 shows the spectral response of the excited waveguide following exposure to a buffer sample spiked with 107 picomolar (pM) CEA. The middle curve shows the response observed for the same membrane/waveguide structure when exposed to a buffer sample, which did not contain CEA, followed by exposure to the detection antibody. This response represents the signal from detection antibody that is nonspecifically bound to the membrane surface. Additional aliquots of detection antibody added to the control experiment were not found to increase the level of nonspecific binding (see FIG. 4). These results allow accurate discrimination of the signal from the CEA antigen binding from nonspecific binding. These experiments can also serve as controls for standard curve titrations. Initial standard curves were completed for CEA on optical waveguides and are shown in FIG. 5. With the current waveguides and membrane architectures, saturation was reached at approximately 2000 femptomoles (fmols) CEA; however the linearity of the curve and saturation point may be expected to be extended in the future as the capture antibody concentration can be expected to be much higher.

The sensitivity limit of the waveguide assay depends on the ability to measure a signal from specific versus nonspecific binding. This detection limit can be lowered by either reducing the nonspecific binding or by introducing a reference channel and reference dye to measure the signal generated by nonspecific binding. It has been demonstrated that uniform and reproducible sensing films and waveguides can be formed to permit accurate measurement of the signal from nonspecific binding. In this way, the signal from nonspecific binding can be subtracted out thereby giving higher sensitivity. Based on the results, it has been established that the current detection limit for CEA at 0.09 nanograms (ng) (this corresponds to 5 pM or 0.9 ng/ml based on the volume of the present sample cell). While it is expected that the current detection limit for CEA can be lowered, the range measured in nipple aspirate fluid for patients suspected of having cancer ranged from 0.34 to 3.76 ng; therefore, there was no need to decrease the level of detectability for CEA but might for other cancer antigens when such an assay is optionally multiplexed for multiple targets. It is also expected that the linear response for CEA can be increased by careful selection of other membrane surfaces, because of the potential for increase in capture antibody concentration on the surface. Currently the assay of the present invention takes about 10 minutes to complete and is from 3 to 4 hours shorter in required time than standard ELISA. It is expected that this approach (subtraction of the signal generated from nonspecific binding) should also be possible for other tumor markers and that the detection limits can be lowered to the mid- to low fM range.

NAF samples were collected from patients undergoing breast biopsies. In order to detect and quantitate CEA in NAF, a nitrocellulose (NC) dot blot assay for CEA was developed. Human serum albumin (HSA), which is found in all NAF samples, was chosen as a reference protein for comparative analysis of patient's samples. NAF was collected from both breasts to test whether the non-malignant breast of a cancer patient would serve as a control and possibly provide a measure of the CEA level expected for normal healthy individuals. However, it was found that both breasts had similar levels of CEA. Because CEA levels are expected to be low in the breasts healthy patients, these results suggest that the disease was present in both breasts despite the absence of observed lesions based on mammography. That suggested it is now critical to enlarge the study to collect NAF from patients with no disease.

Since it was anticipated that the amount of CEA present on the NC blots would be as low as 0.5 ng, a standard curve was run from 0.156-160 ng. The CEA was diluted in 0.05 mg/mL ovalbumin to maintain a constant amount of protein. The standards also contained HSA in the range 0.018-18.2 micrograms ($\mu$g) so that HSA could be detected by a conventional enzyme-immunoassay. Accordingly, CEA standards were spotted in triplicate on nitrocellulose, dried at 65° C. for ten minutes, and blocked for 90 minutes at room temperature (10% dried skim milk/0.1% Tween 20). The membranes were subsequently washed, incubated with T84.1 (mouse anti-CEA antibody, 1:4000 dilution) for 45 minutes at room temperature, washed and incubated with goat anti-mouse IgG-HRP conjugate (1:3000) for 45 minutes. Dot blots were developed for five minutes with chemiluminescence substrate (Pierce CL). The filters were exposed to Biomax film for two and ten minutes. The developed films were scanned on a BioRad integrating densitometer.

Following CEA detection, the filters were further developed to detect HSA. Briefly, the filters were stripped for 1 hour at room temperature with a pre-warmed (65° C.) solution of 2% SDS, 100 mM $\beta$-mercaptoethanol, and 65 mM Tris-HC1(pH 6.8). The stripped blots were monitored to verify antibody removal was complete. The stripped blots were blocked as described above, washed, incubated with a rabbit anti-HSA antibody (1:2000) for 45 minutes at room temperature, washed, and incubated with goat anti-rabbit antibody-AP conjugate (1:5000) for 45 minutes at room temperature. The blots were then washed and developed with NBT/BCIP (Nitro-Blue Tetrazolium Chloride/ 5-Bromo-4-Chloro-3'-Indolyphosphate p-Toluidine Salt, Pierce Chem. Co.) for 5 minutes at room temperature. The filters were developed and analyzed using the densitometer. The results demonstrated a linear response for CEA from 0.31-160 ng, and for HSA from 0.036-36.4 $\mu$g when plotted on a semi-log plot. Representative results for 11 patients were compared with a HSA standard.

As noted above, NAF was collected from 40 patients under an IRB approved protocol. The NAF was diluted 1:50-1:100 in PBS and 2 $\mu$L was spotted onto NC membranes in triplicate (an example of raw data was collected from the first 11 patients and compared with HSA standards). Detection of CEA and HSA was performed as described above. CEA values were compared pair wise from both breasts normalized to the same value of HSA. Twenty-three out of forty patients had successful collections from both breasts. In addition, each patient had serum CEA measured by the Abbott clinical assay, and pathology reports on breast biopsies were also collected.

Of the 23/40 patients who had pair wise samples collected the range of CEA was from 0.34-3.75 ng (roughly 3.4 to 37 ng/ml concentration). Nineteen out of twenty three had a proven diagnosis of cancer as determined by a positive biopsy result. While 4 of the 23 were negative, it is still possible that they too have breast cancer. While there was no clear cutoff of "normal" vs. cancer, it should be noted that each of the patients were admitted to the study because of a suspected lesion, and, as noted above, all of these patients may have cancer. Therefore, one of the goals of this application is to obtain a normal cohort of NAF to resolve this issue. Of the 19 patients with proven cancer and who had NAF from both breasts, 8/19 (42%) had higher CEA values in the breast with a proven diagnosis of cancer; however, this comparison did not reach statistical significance (p=0.64, Table 1). While larger numbers are required to determine if the contralateral breast can serve as a control for the affected breast, the tentative conclusion is that it does not, at least for the use of CEA as a tumor marker. A comparison of the results for all invasive ductal carcinoma versus all non-invasive carcinomas (DCIS) are statistically significant (p=0.001, Table 1). Thus, it is concluded that the CEA assay for NAF has the potential to distinguish between these two important groups. Since the average values for invasive versus non-invasive are lower, it will be important to demonstrate that values for normal breast are even lower than both groups studied. Considering that CEA is absent in normal breast, this is a reasonable expectation. If this is not observed, then a different tumor marker must be used to make the initial diagnosis at which point CEA can be used to distinguish between invasive and non-invasive cancer.

TABLE 1

| Sample | n | Mean CEA (ng) | Std Dev | P-value |
|---|---|---|---|---|
| Bilateral tumor | 19 | 1.006 | 0.830 | |
| Bilateral control | 19 | 0.865 | 1.015 | 0.6419 |
| Bilateral invasive affected | 12 | 0.69 | 0.321 | |
| bilateral invasive non affected | 12 | 0.556 | 0.639 | 0.3784 |
| bilateral non-invasive affected | 6 | 1.685 | 1.182 | |
| bilateral non-invasive non affected | 6 | 1.61 | 1.364 | 0.9209 |
| all tumor | 50 | 1.063 | 1.025 | |
| all non-tumor | 11 | 0.742 | 0.589 | 0.3222 |
| all non-invasive tumor | 14 | 1.797 | 1.271 | |
| all invasive tumor | 36 | 0.777 | 0.756 | 0.001 |
| all non-invasive tumor | 14 | 1.797 | 1.271 | 0.0183 |

Data from NAF was compared in several ways. In the first pairwise analysis, all NAF samples obtained from patients who had tumor in one breast were compared, but none in the other (but it should be noted that the contralateral breast was not biopsied). In this case the p value (0.6419) demonstrates no statistical difference. In the second group invasive affected breast vs. non-affected (the contralateral control) were compared and again find no statistical difference. In the third group non-invasive affected vs. the contralateral breast were compared and find no statistical difference. Finally, all tumor vs. all non tumor were compared and see no statistical difference. Thus, there is no evidence that CEA varies between the two breasts in all tumors studied whether invasive or non-invasive. For this reason, all non-invasive vs. all invasive cancers (ignoring contralateral breast) were compared and a highly significant result was observed when the two groups are compared in either direction. It was concluded that CEA is higher in non-invasive vs. invasive cancers and that it is elevated equally in both breasts. These are very interesting conclusions in that the first finding agrees with immunohistochemistry: non-invasive breast cancers are high in CEA (>95%) and drop with invasive cancers (ca 50%). The second conclusion, that CEA levels are similar between breasts, is new and had been generally suspected by pathologists.

It has been demonstrated that NAF can be collected for the direct assay of CEA using HSA as a standard. CEA has been detected at low levels in NAF from both malignant and normal breasts. For the limited sample studied, no clear cutoff between malignant versus normal breasts has been observed, although the sample size may be too low to finalize this conclusion and because there was an insufficient control population. When comparing non-invasive versus invasive ductal carcinoma, highly significant results were obtained. If further studies demonstrate that CEA levels are low in normal breasts, then the rise in concentration in non-invasive ductal carcinoma this change can be used as an early sign of a malignant condition. Furthermore, a subsequent drop in CEA would signal a change from non-invasive to invasive carcinoma, an important result. In the present study, no normal healthy individuals were included in the pool of patients. While it is not expected to find CEA levels in normal healthy individuals outside the range established in this study, some uncertainty remains.

Biopsies from the patients were used to establish a positive diagnosis of breast cancer (Table 1). In addition, the specimens were stained with anti-CEA antibody T84.66 to determine if the tissue specimen was positive for CEA. Although it is difficult to define CEA cut-off values for both NAF and tissue specimens at this time, it can be stated with some confidence that NAF samples that had CEA values >1 ng had biopsies that stained strongly for CEA while those <1 ng were only weakly stained. In addition, the strongest staining specimens were those containing DCIS or atypical ductal hyperplasia as mentioned in the introduction. Examples of CEA staining of patient biopsy tissue were developed.

Although the present invention has been described with reference to specific details, it is not intended that such details should be regarded as limitations upon the scope of the invention, except as and to the extent that they are included in the accompanying claims.

what is claimed is:

1. A sandwich assay sensor element comprising: recognition ligands for carcinoembryonic antigen (CEA) bound to a film on a single mode planar optical waveguide, said film selected from the group consisting of a membrane, a polymerized bilayer membrane, and a self-assembled monolayer containing polyethylene glycol or polypropylene glycol groups therein.

2. A sandwich assay sensor element comprising: recognition ligands for carcinoembryonic antigen (CEA) bound to a film on a single mode planar optical waveguide, said film selected from the group consisting of a membrane, a polymerized bilayer membrane, and a self-assembled monolayer containing polyethylene glycol or polypropylene glycol groups therein, wherein the recognition ligands are selected from the group consisting of antibodies T84.66 and T84.1, said T84.66 antibody capable of binding to an A3 epitope of carcinoembryonic antigen (CEA) and said T84.1 antibody capable of binding to a N epitope of CEA.

3. The sandwich assay sensor element of claim 1 wherein the membrane is a supported bilayer membrane.

4. The sandwich assay sensor element of claim 1 wherein the recognition ligands are bound to the film by trifunctional anchoring molecules including a fluorescent reporter molecule thereon.

5. The sandwich assay sensor element of claim 1 wherein the film is a membrane and the recognition ligands are bound to the film by trifunctional membrane anchoring molecules including a fluorescent reporter molecule thereon.

6. The sandwich assay sensor element of claim 1 wherein the film is a membrane and the recognition ligands are bound to the film by trifunctional membrane anchoring molecules including a secondary recognition ligand thereon.

7. The sandwich assay sensor element of claim 1 wherein the recognition ligands are movably situated within the fluid membrane through multifunctional membrane anchoring molecules.

8. A sandwich assay process for detecting the presence of a biological target of carcinoembryonic antigen (CEA) comprising:
   injecting a biological target-containing sample into a sensor cell including recognition ligands for carcinoembryonic antigen (CEA) bound to a film on a single mode 5 planar optical waveguide, said film selected from the group consisting of a membrane, a polymerized bilayer membrane, and a self-assembled monolayer containing polethylene glycol or polypropylene glycol groups therein, the recognition ligands capable of binding to carcinoembryonic antigen (CEA);
   maintaining the biological target-containing sample within the sensor cell for a time sufficient for a binding event to occur between carcinoembryonic antigen (CEA) within the sample and the recognition ligands capable of binding to said carcinoembryonic antigen (CEA);
   injecting a solution including a reporter ligand into the sensor cell; and,
   interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal.

9. A sandwich assay process for detecting the presence of a biological target of carcinoembryonic antigen (CEA) comprising:
   injecting a biological target-containing sample into a sensor cell including recognition ligands for carcinoembryonic antigen (CEA) bound to a film on a single mode 5 planar optical wave guide, said film selected from the group consisting of a membrane, a polymerized bilayer membrane, and a self-assembled monolayer containing polyethylene glycol or polypropylene glycol groups therein, the recognition ligands capable of binding to carcinoembryonic antigen (CEA);
   maintaining the biological target-containing sample within the sensor cell for a time sufficient for a binding event to occur between carcinoembryonic antigen (CEA) within the sample and the recognition ligands capable of binding to said carcinoembryonic antigen (CEA);
   injecting a solution including a reporter ligand into the sensor cell; and, interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal,
   wherein the recognition ligands are selected from the group consisting of antibodies T84.66 and T84.1, said T84.66 antibody capable of binding to an A3 epitope of carcinoembryonic antigen (CEA) and said T84.1 antibody capable of binding to a N epitope of CEA.

10. The process of claim 8 wherein the membrane is a supported bilayer membrane.

11. The process of claim 8 further including injecting a wash solution into the sensor cell to remove excess biological target after the sample is maintained for time sufficient for a binding event to occur.

12. The process of claim 8 wherein the recognition ligands are bound to the film by trifunctional anchoring molecules including a fluorescent reporter molecule thereon.

13. The process of claim 8 wherein the film is a membrane and the recognition ligands are bound to the film by trifunctional membrane anchoring molecules including a reporter molecule thereon.

14. The process of claim 8 wherein the film is a membrane and the recognition ligands are bound to the film by trifunctional membrane anchoring molecules including a secondary recognition ligand thereon.

15. The process of claim 8 wherein the recognition ligands are movably situated within the fluid membrane through multifunctional membrane anchoring molecules.

16. A sandwich assay process for detecting the presence of a biological target of carcinoembryonic antigen (CEA) comprising:
   injecting a biological target-containing sample into a sensor cell including recognition ligands for carcinoembryonic antigen (CEA) bound to a film on a single mode 5 planar optical waveguide, said film selected from the group consisting of a membrane, a polymerized bilayer membrane, and a self-assembled monolayer containing polyethylene glycol or polypropylene glycol groups therein, the recognition ligands capable of binding to carcinoembryonic antigen (CEA);
   maintaining the biological target-containing sample within the sensor cell for a time sufficient for a binding event to occur between carcinoembryonic antigen (CEA) within the sample and the recognition ligands capable of binding to said carcinoembryonic antigen (CEA);
   injecting a solution including a reporter ligand into the sensor cell; and, interrogating the biological target-containing sample within the sensor cell with excitation light from the waveguide, the excitation light provided by an evanescent field of the single mode penetrating into the biological target-containing sample to a distance of less than about 200 nanometers from the waveguide thereby interacting with any bound reporter ligand within a distance of less than about 200 nanometers from the waveguide and resulting in a detectable signal,
   wherein the assay process further includes distinguishing between ductal carcinoma insitu (DCIS) and invasive ductal carcinoma from the detectable signal.

17. The process of claim 8 wherein the reporter ligands include attached materials for fluorescence or scatter product detection.

18. A sandwich assay process for detecting the presence of carcinoembryonic antigen (CEA) including:
   injecting a solution including a biological target-containing sample and a reporter ligand into a sensor cell including recognition ligands for carcinoembryonic antigen (CEA) bound to a film on a single mode planar optical waveguide, said film selected from the group consisting of a membrane, a polymerized bilayer membrane, and a self-assembled monolayer containing polyethylene glycol or polypropylene glycol groups therein, the recognition ligand capable of binding to CEA;
   maintaining the biological target-containing sample within the sensor cell for a time sufficient for a binding event to occur between CEA within the sample and the recognition ligands capable of binding to CEA;
   injecting a wash solution into the sensor cell to remove excess biological target and excess reporter ligand; and,
   interrogating the biological target-containing sample within the sensor cell with excitation light from the waveguide, the excitation light provided by an evanescent field of the single mode penetrating into the biological target-containing sample, to a distance of less than about 200 nanometers from the waveguide thereby interacting with any bound reporter ligand within a distance of less than about 200 nanometers from the waveguide and resulting in a detectable signal.

19. A sandwich assay process for detecting the presence of carcinoembryonic antigen (CEA) including:
   injecting a solution including a biological target-containing sample and a reporter ligand into a sensor cell including recognition ligands for carcinoembryonic antigen (CEA) bound to a film on a single mode planar optical waveguide, said film selected from the group consisting of a membrane, a polymerized bilayer membrane, and a self-assembled monolayer containing polyethylene glycol or polypropylene glycol groups therein, the recognition ligand capable of binding to CEA;
   maintaining the biological target-containing sample within the sensor cell for a time sufficient for a binding event to occur between CEA within the sample and the recognition ligands capable of binding to CEA;
   injecting a wash solution into the sensor cell to remove excess biological target and excess reporter ligand; and,
   interrogating the biological target-containing sample within the sensor cell with excitation light from the waveguide, the excitation light provided by an evanescent field of the single mode penetrating into the biological target-containing sample, to a distance of less than about 200 nanometers from the waveguide thereby interacting with any bound reporter ligand within a distance of less than about 200 nanometers from the waveguide and resulting in a detectable signal;
   wherein the recognition ligands are selected from the group consisting of antibodies T84.66 and T84.1, said T84.66 antibody capable of binding to an A3 epitope of carcinoembryonic antigen (CEA) and said T84.1 antibody capable of binding to a N epitope of CEA.

20. The process of claim 18 wherein the membrane is a supported bilayer membrane.

21. The process of claim 18 wherein the recognition ligands are bound to the film by trifunctional anchoring molecules including a reporter molecule thereon.

22. The process of claim 18 wherein the film is a membrane and the recognition ligands are bound to the film by trifunctional membrane anchoring molecules including a reporter molecule thereon.

23. The process of claim 18 wherein the film is a membrane and the recognition ligands are bound to the film by trifunctional membrane anchoring molecules including a secondary recognition ligand thereon.

24. The process of claim 18 wherein the reporter ligands include attached materials for fluorescence or scatter product detection.

25. The process of claim 18 wherein the recognition ligands are movably situated within the fluid membrane through multifunctional membrane anchoring molecules.

* * * * *